United States Patent [19]
Simonyi et al.

[11] Patent Number: 6,123,687
[45] Date of Patent: Sep. 26, 2000

[54] CELL SEPARATION DEVICE AND METERING SYRINGE

[75] Inventors: Victor Simonyi, Berkeley; Olexander Hnojewyj, Saratoga; James Duronio, Mountain View; Abigail Freeman, Fremont; Dominick G. Esposito, Los Almos; Bonnie G. Stearns, Cupertino; Stephen Schoenberg, Redwood City, all of Calif.

[73] Assignee: Cohesion Technologies, Inc., Palo Alto, Calif.

[21] Appl. No.: 09/032,347

[22] Filed: Feb. 27, 1998

Related U.S. Application Data

[63] Continuation-in-part of application No. 08/741,233, Oct. 30, 1996, application No. 08/886,958, Jul. 2, 1997, abandoned, and application No. 08/886,957, Jul. 2, 1997.

[51] Int. Cl.[7] .................................................. A61M 5/00
[52] U.S. Cl. ............................................. 604/207; 604/211
[58] Field of Search ....................................... 604/207, 208, 604/211, 218, 224, 187

[56] References Cited

U.S. PATENT DOCUMENTS

| | | |
|---|---|---|
| 4,498,904 | 2/1985 | Turner et al. .............................. 604/211 |
| 4,744,955 | 5/1988 | Shapiro . |
| 5,017,190 | 5/1991 | Simon et al. . |
| 5,292,318 | 3/1994 | Haber et al. . |
| 5,300,041 | 4/1994 | Haber et al. .............................. 604/207 |
| 5,454,793 | 10/1995 | Levander et al. . |
| 5,728,075 | 3/1998 | Levander ................................. 604/211 |

FOREIGN PATENT DOCUMENTS

| | | |
|---|---|---|
| 840 257 | 4/1939 | France . |
| 2 612 782 | 3/1987 | France . |
| 807 113 | 7/1949 | Germany . |
| 121 823 | 11/1970 | United Kingdom . |
| WO 88/07874 | 10/1988 | WIPO . |

*Primary Examiner*—John D. Yasko
*Attorney, Agent, or Firm*—Pennie & Edmonds LLP

[57] ABSTRACT

A device for sample collection, sample separation and for aseptically, controllably and precisely transferring at least one of the separated portions is disclosed. The device utilizes a metering syringe to collect a sample, such as blood, the metering syringe with the sample therein is centrifuged, the metering syringe is connected to a sterile syringe contained within sterile packaging, the metering syringe is used to controllably, precisely and aseptically meter a separated portion into the sterile syringe, the sterile syringe with the separated portion therein is then given to appropriate personnel within a sterile field without performing any further transferring steps.

20 Claims, 6 Drawing Sheets

CELL SEPARATION DEVICE AND METERING SYRINGE

RELATED APPLICATIONS

This is a continuation-in-part of application Ser. No. 08/741,233 filed Oct. 30, 1996, Ser. No. 08/886,958 filed Jul. 2, 1997, abandoned, and Ser. No. 08/886,957 filed Jul. 2, 1997.

FIELD OF THE INVENTION

The present invention generally relates to a syringe-based fluid separation system, however, various components of the invention may be used apart from the system as described herein. More specifically, the present invention relates to an apparatus and method of using a syringe for obtaining a biological or other fluid sample, centrifuging the syringe to separate the suspended solids from the fluid portion and with a high degree of control and accuracy, transferring the separate portions to different processing vessels.

BACKGROUND OF THE INVENTION

The process of obtaining a biological or other fluid sample, such as blood, and the subsequent centrifugation process generally requires multiple steps and devices, which include transferring the sample from the sampling syringe to a separate centrifugation tube, centrifugation of the sample and then decanting the separated portions to different vessels for further processing. The increase in handling time by medical personnel and the use of multiple devices, as opposed to a single device, increases the overall inconvenience, costs and time necessary to perform the procedure. More importantly, the increase in sample handling increases the risk of contaminating the sample thus, increasing the risk of contaminating later process steps-e.g., contaminating the sterile operating field wherein the contaminated plasma would be used. Furthermore, the increase in handling increases the exposure of medical personnel to whatever infectious agents the blood sample may contain.

Common prior art collection-separation-transfer systems generally use multiple devices for sample collection, separation and transfer of the plasma portion. For example U.S. Pat. No. 3,654,925 discloses using a vacuum tube to collect the sample; centrifuging the sample in a cell-collection tube coupled to the vacuum tube via an intermediate needle assembly; and transferring the plasma portion using a non-sterile syringe with a needle. The device disclosed in the '925 patent also does not allow precise transfer of all of the plasma from the separated blood sample. Another example, U.S. Pat. No. 3,586,064, discloses collecting the sample in a vacuum tube; centrifuging the vacuum tube to separate the sample; opening the vacuum tube to the atmosphere; collecting the plasma portion with a separate collection device, also opened to the atmosphere; and transferring the plasma from the collection device with a separate syringe. In both of these examples multiple steps and devices are required to accomplish sample collection, sample separation and transfer of the plasma portion. Neither example discloses an apparatus or method to precisely, controllably and aseptically transfer the entire plasma portion of the separated sample. Furthermore, neither example discloses an apparatus or method to transfer the fluid from a non-sterile environment to a sterile environment without performing an additional fluid transfer step.

Metered transfer syringes also exist in the prior art and generally allow repetitive and accurate withdrawal and transfer of an aliquot from a bulk source. For example, U.S. Pat. No. 4,744,955 to Shapiro discloses a spring biased plunger assembly disposed within an adjustable syringe barrel assembly. The adjustable syringe barrel assembly is a hollow cylinder and a standard syringe barrel axially aligned and retained together by complementary screw threads. The spring biases against the plunger assembly which forces the plunger assembly out of the syringe barrel a fixed distance. The volume of the aliquot is controlled by relative rotation of the syringe barrel and cylinder. These metering syringes, exemplified by the '955 device, require multiple devices to accomplish sample collection, sample separation and aseptic transfer of the plasma portion of a blood sample. Due to the arrangement of the plunger and spring, such a device cannot be effectively centrifuged to allow for the ejection of the plasma fraction.

Use of the plasma portion in a sterile operating field necessitates that the collection, separation and transferring steps occur without contaminating the sample, plasma or transferring vessel. However, prior art systems have not achieved the simplicity in processing, as contemplated herein, while maintaining the necessary aseptic conditions.

SUMMARY OF THE INVENTION

In view of the above problems and disadvantages of the prior art, it is an object of the present invention to provide an apparatus for blood withdrawal, sample centrifugation and transfer of the separated plasma portion to a separate vessel for further processing, thus decreasing handling by medical personnel, reducing the risks of contamination, minimizing the number of devices necessary for the process and minimizing the exposure of medical personnel to the blood sample.

It is a further object of the present invention to provide an apparatus for blood withdrawal, sample centrifugation and transfer of the separated plasma portion to a separate vessel for further processing wherein the apparatus has a mechanism for controllably, accurately and aseptically transferring the desired amount of plasma to the separate vessel.

It is yet a further object of the present invention to aseptically transfer the separated plasma portion to a sterile syringe contained within sterile packaging in a non-sterile environment. The fluid filled syringe can then be transferred to personnel within the sterile field by simply opening the packaging and allowing the personnel to aseptically remove the sterile fluid filled syringe.

A preferred embodiment of the present invention includes a syringe equipped with a metering mechanism to advance the syringe stopper with a high degree of control and accuracy independent of the standard plunger rod mechanism. The interior of the syringe is preferably sterile and contains a predetermined amount of anticoagulant, such as EDTA or sodium citrate. The metering mechanism may include a threaded sleeve placed over the syringe body.

Preferably, the syringe is used to obtain a blood sample, the plunger rod is detached and the metering syringe is placed in a centrifuge, wherein centrifugation separates the plasma from the blood cells. The metering mechanism is then used to accurately transfer only the plasma portion to a sterile syringe contained within a sterile syringe packaging, which can be handled without concern for contaminating the sterility of the syringe or its contents. The sterile syringe with the plasma portion can then be transferred to personnel within the sterile field by simply opening the packaging and allowing the personnel to aseptically remove the sterile syringe containing the plasma portion of the original blood sample. Therefore, the sample collection-separation-transfer system of the present invention requires fewer process steps to collect a sample, separate the sample and transfer a separated portion from a non-sterile environment to a sterile field such as an operating table.

Because of the need to minimize the risk of sample contamination, the present invention also includes a specially designed syringe cap to provide a sterile barrier between the interior and exterior of the syringe. The cap allows the user to better manipulate the sampling-separation syringe without increasing the risk of contaminating the sample or the inside of the syringe. Furthermore, the user may even drop the cap and still be able to use the cap without contaminating the sample or the syringe.

The separation system of the present invention is described herein in terms of utilizing blood as the fluid sample. However, other biological and non-biological fluid samples may readily be used in the separation system as will be apparent to those skilled in the art. The separation system of the present invention is also described herein in terms of transferring the separated fluid to a sterile syringe within a sterile package. However, other vessels, sterile or not, may be used into which to transfer the separated fluid as will be readily apparent to those skilled in the art.

DETAILED DESCRIPTION OF THE INVENTION

Figure 1:
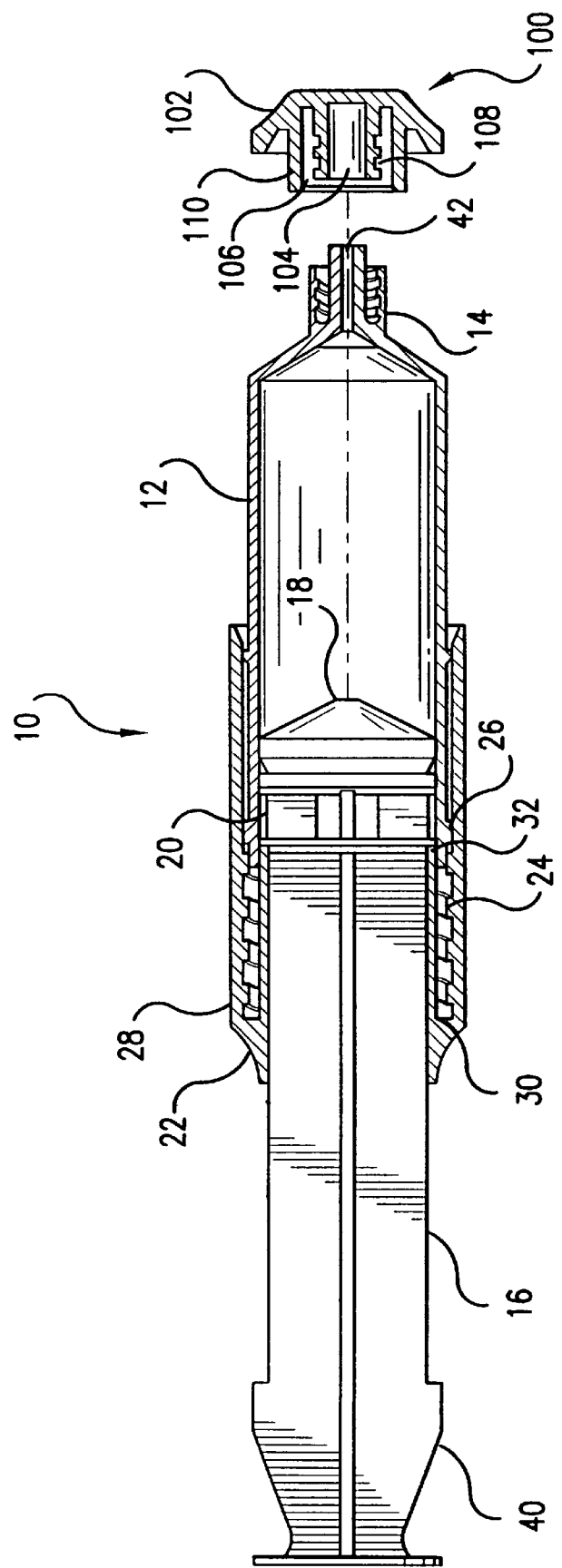
FIG. 1 is a partial cross-sectional view of a metering syringe cell separator device according to an embodiment of the present invention.
Figure 2:
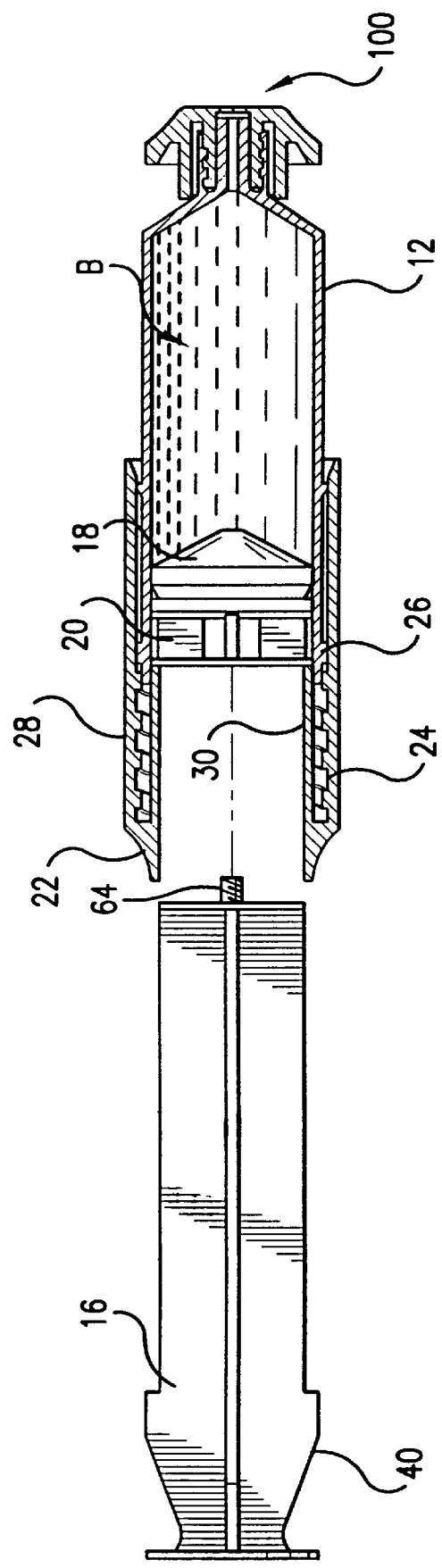
FIG. 2 is a partial cross-sectional view of the metering syringe cell separator device of FIG. 1 containing a blood sample prior to centrifugation of the sample.

FIGS. 1 and 2 illustrate an embodiment of the present invention comprising, a metering syringe 10 which includes syringe body 12, needle fitting 14, plunger rod 16, stopper 18 attached to stopper support member 20, metering knob 22 and sterile cap 100. Plunger rod 16 is preferably detachably connected to stopper support member 20 via threaded portion 66. The component parts of metering syringe 10 are made from a suitable material known to the skilled artisan, preferably moldable medical grade plastic, polypropylene being one example.

In a preferred embodiment, metering knob 22 defines annular space 24 configured to slidingly engage syringe body 12. Preferably, annular space 24 is threaded to engage matching threads 26 on syringe body 12. However, those skilled in the art will appreciate that other mechanisms may be adapted to the present invention to slidingly engage annular space 24 with syringe body 12. Annular space 24 has an outer wall 28 and an inner wall 30. Preferably, outer wall 28 extends beyond annular space 24 to support syringe body 12. Inner wall 30 forms edge 32 at the open end of annular space 24. Edge 32 abuts stopper support member 20 such that advancement of metering knob 22 over syringe body 12 causes edge 32 to bear against support member 20 and advance stopper 18 towards the conical end of syringe body 12. The wall of syringe body 12 is received in annular space 24 as metering knob 22 is advanced. Edge 32 is preferably not attached to support member 20 and thus may advance stopper 18, but not withdraw it. Withdrawal of stopper 18 may be accomplished via plunger rod 16 in a known manner, unless metering knob 22 is in an advanced position, wherein edge 32 prevents the withdrawal of syringe stopper 18.

Figure 5:
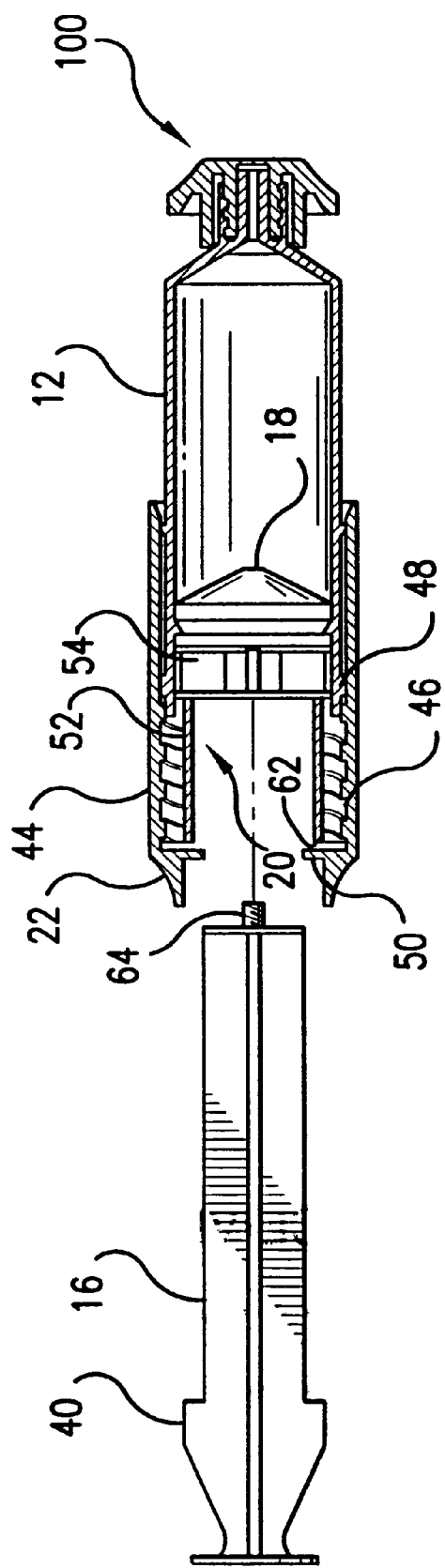
FIG. 5 is partial cross-sectional view of a metering syringe cell separator device according to an alternative embodiment of the present invention.

In an alternative embodiment, shown in FIG. 5, metering knob 22 preferably comprises hollow cylinder 44, with internal threads 46 which engage external threads 48 on syringe body 12. Inward abutment 50 is provided to abut stopper support member 20, such that advancement of metering knob 22 causes inward abutment 50 to bear against support member 20 and advance stopper 18. Stopper support member 20 preferably comprises hollow member 52 with a closed end 54 that attaches to stopper 18 and an open end 62 which abuts against inward abutment 50 as previously described. A skilled artisan will readily recognize that stopper support member may take many alternative configurations without departing from the scope of the present invention. Inward abutment 50 preferably extends around the interior periphery of hollow cylinder 44, although a skilled artisan will readily recognize alternative configurations for inward abutment 50. Inward abutment 50 is preferably not attached to stopper support member, thus preferably metering knob 22 may advance stopper 18 but not withdraw it.

Figure 6:
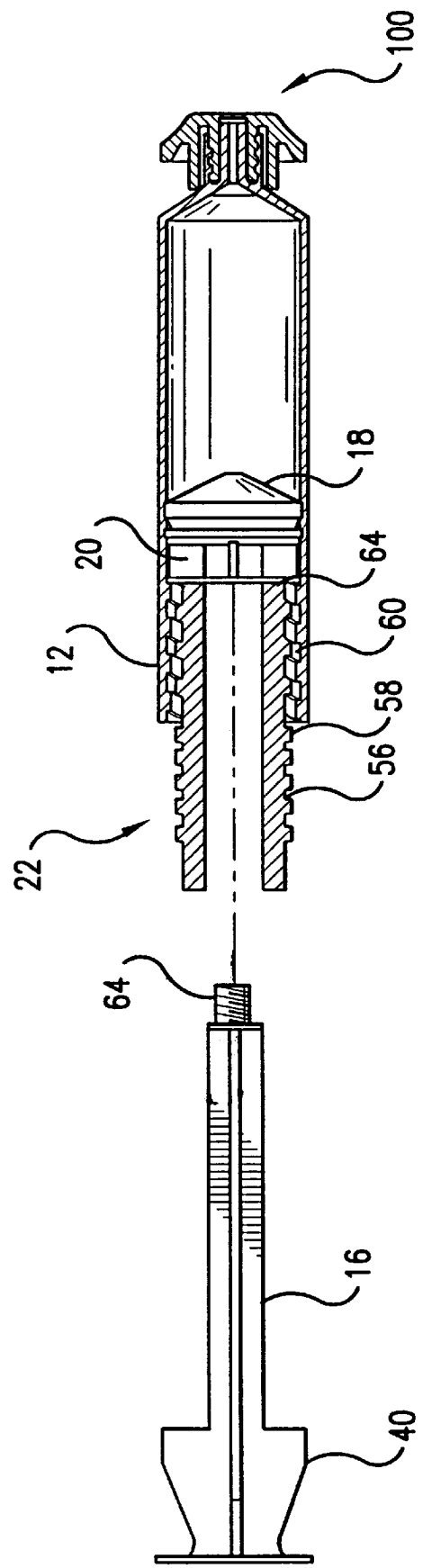
FIG. 6 is partial cross-sectional view of a metering syringe cell separator device according to another alternative embodiment of the present invention.

In another alternative embodiment, shown in FIG. 6, metering knob 22 preferably comprises hollow cylinder 56 with external threads 58 which engage internal threads 60 on syringe body 12. In this alternative embodiment, hollow cylinder 56 passes into syringe body 12 and abuts stopper support member 20 at point 64, as shown in FIG. 6. Stopper support member 20 is preferably a standard syringe stopper support member, although a skilled artisan will readily recognize alternative configurations without departing from the scope of the present invention. Hollow cylinder 56 is preferably not attached to stopper support member, thus preferably metering knob 22 may advance stopper 18 but not withdraw it.

In a preferred embodiment, syringe 10 is shipped to a user, as depicted in FIG. 1, with stopper 18, plunger rod 26 and metering knob 22 all in their respective "withdrawn" positions. The interior of syringe body 12 is preferably sterile and contains a predetermined amount of sterile anticoagulant (not shown), such as EDTA or sodium citrate, sterile cap 100 covers and seals fitting 14. Sterile cap 100 (see FIG. 1) comprises hollow cylinder 102 having tapered hollow cylindrical cavity 104 centrally disposed. Cylindrical cavity 104 is surrounded by annular channel 106 and annular channel 106 defines inner wall 108 and outer wall 110. Inner wall 108 is a cylindrical wall that has threads 112 or other means to mate with fitting 14. Outer wall 110 is higher relative to inner wall 108 and serves to protect inner wall 108 from becoming contaminated in the event cap 100 is dropped or placed upside down. Outer wall 110 also protects needle fitting 14 from contamination when cap 100 is locked into place.

According to a preferred embodiment, appropriate personnel use the apparatus to obtain a blood sample, separate the blood sample within the device and aseptically transfer the plasma portion to a sterile field. To draw the blood sample, the user holds syringe 10 upright, i.e., tip 14 up plunger rod 16 down, removes sterile cap 100, advances stopper 18, attaches fitting 14 to a sample source, e.g., a needle or IV line fitting, and in a known manner draws a blood sample. Tab stops 40, attached to plunger rod 16, have been provided in a preferred embodiment to prevent a user from mistakenly ejecting anticoagulant before drawing the blood sample. However, a person skilled in the art will recognize alternatives to using tab stops 40 to prevent the accidental ejection of anticoagulant.

Figure 3:
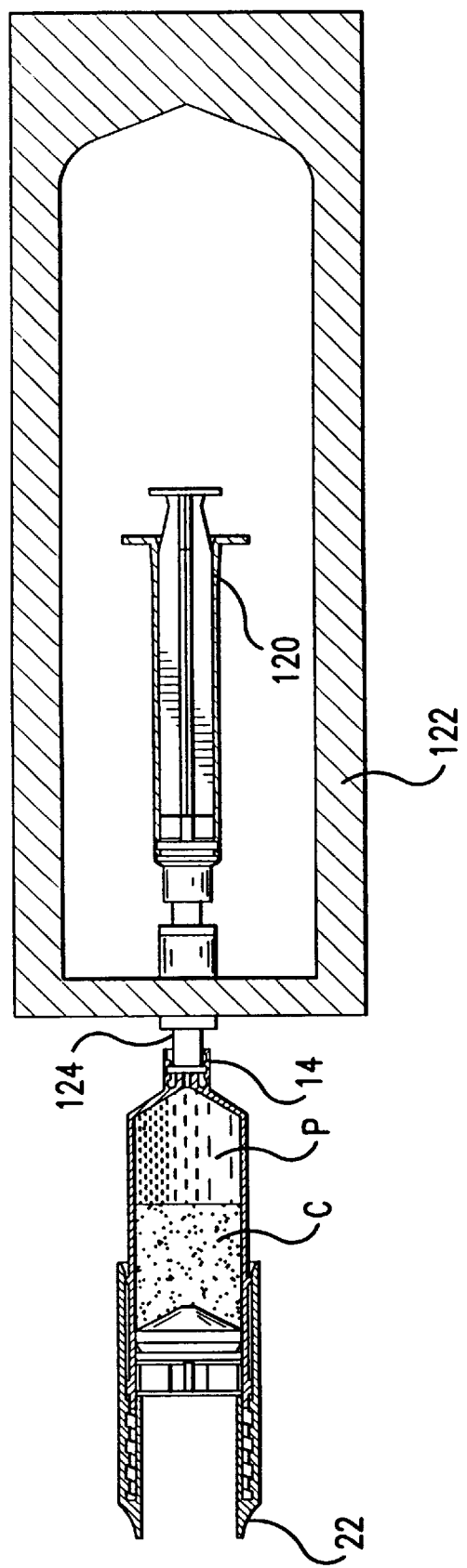
FIG. 3 is a partial cross-sectional view of the metering syringe cell separator device of FIG. 2 containing the separated plasma and blood cell fractions ready for metered transfer of the plasma portion to a sterile syringe contained within a sterile package.

After drawing the sample, the user removes fitting 14 from the sample source, replaces sterile cap 100, mixes the blood with anticoagulant by several inversions and removes plunger rod 16 from stopper support member 20. This latter configuration is best depicted in FIG. 2 where B represents the blood sample. The user places metering syringe 10, without plunger rod 16, into a centrifuge with sterile cap 100 pointing upwards and spins the device to separate the blood cells. During centrifugation, denser cells C separate and move towards stopper 18 and plasma P remains on top as depicted in FIG. 3. To transfer the plasma, syringe 10 is removed from the centrifuge, held upright, sterile cap 100 is removed and metering knob 22 is rotated to controllably and precisely advance stopper 18 to eject plasma P.

Figure 4:
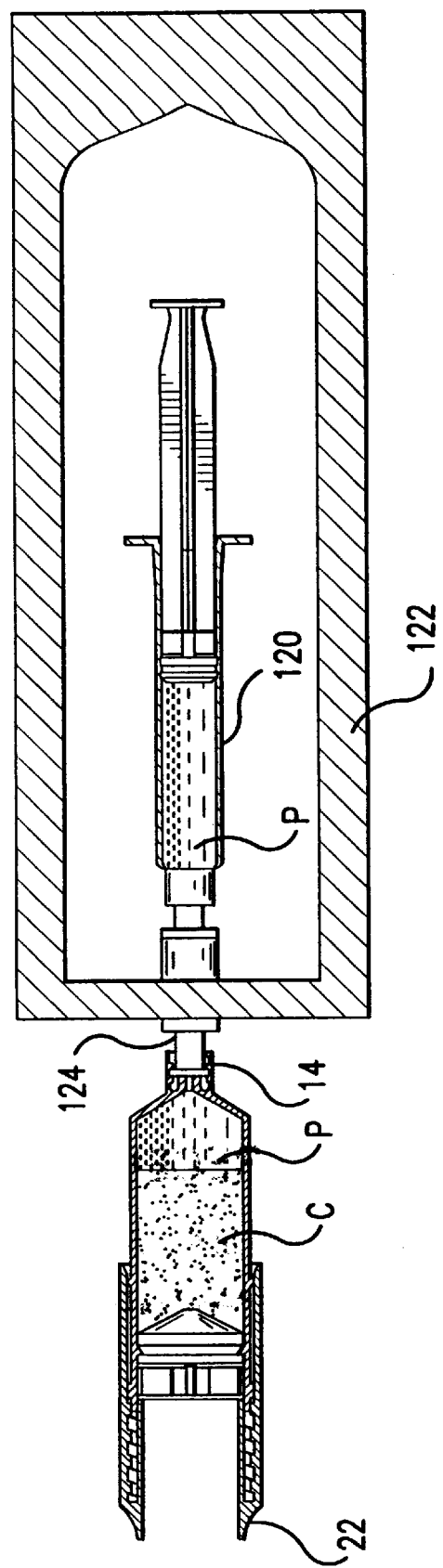
FIG. 4 is a partial cross-sectional view of the metering syringe cell separator device of FIG. 3 after plasma has been transferred to the sterile syringe contained within the sterile package.

Once plasma P has been separated, it may be desirable to deliver the plasma into a sterile field for use in a variety of applications. This is conveniently accomplished according to the present invention by transferring the plasma portion to a sterile syringe in a sterile packaging as shown in FIGS. 3 and 4. In this embodiment, fitting 14 is connected to mating fitting 124 of sterile syringe 120 within packaging 122. The plasma fraction P is ejected from syringe 10, as described above, into sterile syringe 120. Packaging 122 may then be opened and sterile syringe 120, containing plasma P, may be passed to a user in a sterile field who unthreads the filled syringe from its fitting and removes the filled syringe. Such sterile packagings and their use are described in greater detail in copending applications Ser. Nos. 08/886,957 and 08/886,958, both filed Jul. 2, 1997, both of which are incorporated by reference herein in their entirety.

In alternative embodiments, annular space 24 can be made to prevent a user from transferring more than a predetermined volume of plasma, thus preventing the accidental transfer of red blood cells to sterile syringe 120. However, as noted one primary advantage of using metering knob 22 is that it provides the user with a high degree of precision and control when transferring plasma P to syringe 120.

Although various embodiments of the present invention have been described, the descriptions are intended to be merely illustrative. Thus, it will be apparent to those skilled in the art that modifications may be made to the embodiments as described without departing from the scope of the claims set forth below. In particular, the various components of the invention described herein may be used separately or apart from other components, or in different combinations, without departing from the invention.

What is claimed is:

1. An apparatus for separating and dispensing fluid fractions, comprising:
    a hollow body with a syringe fitting at a first end and an open second end;
    a stopper assembly movably disposed within said hollow body comprising a stopper attached to a first end of a stopper support member;
    a metering knob configured to engage the open end of said hollow body and cooperate with a second end of the stopper support member to advance the stopper assembly within the hollow body; and
    a plunger rod detachably connected to said stopper support member for advancing and withdrawing the stopper assembly within the hollow body.

2. The apparatus according to claim 1, further comprising a threaded connection between the hollow body and the metering knob to facilitate movement of the stopper assembly.

3. The apparatus according to claim 2, wherein:
    the hollow body comprises a syringe body;
    the metering knob comprises a hollow member disposed over the open end of said syringe body, wherein said hollow member has an inwardly extending abutment configured to abut said stopper support member, and wherein said hollow member defines a central opening through which said detachable plunger rod passes for connection to said stopper support member; and
    the threaded connection comprises an external thread element disposed at the open end of said syringe body and an internal thread element on the inside wall portion of the hollow member disposed before said abutment.

4. The apparatus according to claim 3, wherein said stopper support member comprises a hollow cylindrical member closed at said first end and open at said second end, wherein said open second end is configured to abut said metering knob, and wherein said metering knob and said stopper support member define a central opening through which said detachable plunger rod passes for connection to said stopper support member.

5. The apparatus according to claim 3, further comprising a cap configured and dimensioned to be placed on said fitting, wherein said cap comprises an inner annular member adapted to seal said fitting and an outer annular member adapted to surround said fitting and prevent contamination thereof.

6. The apparatus according to claim 3, further comprising:
    a second syringe having a syringe barrel and a syringe fitting coupled to the syringe barrel;
    a sheath sealingly enclosing the second syringe and having an opening, the opening being defined by a surrounding edge portion of the sheath; and
    a fitting member sealingly fixed with the surrounding edge portion of the sheath to form an enclosed syringe chamber housing said second syringe, said fitting member being removably connectable to both said syringe fitting and said second syringe fitting to provide fluid communication between said syringes.

7. The apparatus according to claim 2, wherein:
    the hollow body comprises a syringe body;
    the metering knob is disposed in the open end of said syringe body and configured to abut said stopper support member; and
    the threaded connection comprises an internal thread element disposed at the open end of said syringe body and an external thread element on the outside portion of the metering knob.

8. The apparatus according to claim 7, wherein said metering knob comprises a hollow member defining a central opening through which said detachable plunger rod passes for connection to said stopper support member.

9. A method for separating fluids into component fractions of varying densities and transferring at least one fraction with a high degree of control and precision, comprising the steps of:

collecting a source fluid in a metering apparatus comprising a hollow body; a stopper assembly slidably disposed within the hollow body; a metering knob mounted on an end of the hollow body and cooperating with the stopper assembly for advancing the stopper assembly within said hollow body;

separating said source fluid into a first fraction having a relatively larger density and a second fraction with a relatively smaller density; and ejecting said second fraction from the hollow body with a high degree of control and precision by rotating said metering knob to advance said stopper assembly.

10. The method according to claim 9, wherein:

the collecting step comprises attaching a plunger rod to said stopper assembly and drawing the source fluid into said hollow body by pulling on the plunger rod; and the separating step comprises detaching said plunger rod, centrifuging said apparatus with the source fluid contained therein to separate the first fraction from the second fraction.

11. The method according to claim 9, further comprising transferring the ejected fraction into a sterile field.

12. The method according to claim 11, wherein said transferring step comprises:

connecting a syringe to said hollow body;

introducing said second fraction into said syringe via said ejecting step; and delivering said syringe into the sterile field.

13. The method according to claim 12, wherein said syringe is contained within a sterile packaging and said delivering comprises:

a non-sterile operator holding the outside of the sterile packaging and opening said package to expose said syringe; and a sterile operator grasping said syringe to remove it and introduce it into the sterile environment.

14. The method according to claim 11, wherein said transferring step comprises:

sterilizing a syringe;

sterilizing a syringe package, which package is adapted to receive and encase the syringe in a sterile manner while permitting operation of the syringe;

enclosing the syringe in the syringe package;

connecting said hollow body to said syringe within said package;

introducing said second fraction into said syringe contained in the syringe package via said ejecting step; and delivering the syringe into a sterile environment by removing the syringe from the syringe package.

15. The method of claim 14, wherein said delivering comprises:

a non-sterile operator holding the outside of the syringe package and opening said package to expose said syringe; and a sterile operator grasping said syringe to remove it and introduce it into the sterile environment.

16. The apparatus according to claim 1, wherein the metering knob has an internal wall disposed inside the hollow body bearing against the second end of said stopper assembly and an outer wall engaging the outside of the hollow body, wherein the inner wall and the outer wall define an annular space.

17. The apparatus according to claim 16, further comprising a threaded connection between the outer wall of the meeting knob and the outside of the hollow body to facilitate advancement of the stopper assembly.

18. The apparatus according to claim 17, wherein the hollow body is a syringe body with a syringe fitting at a first end and an open second end and said metering knob defines a central opening through which said plunger rod passes for connection to the second end of the stopper support member.

19. The apparatus according to claim 18, further comprising:

a second syringe having a syringe barrel and a second syringe fitting coupled to the syringe barrel;

a sheath sealingly enclosing the second syringe and having an opening, the opening being defined by a surrounding edge portion of the sheath; and a fitting member sealingly fixed with the surrounding edge portion of the sheath to form an enclosed syringe chamber housing said second syringe, said fitting member being removably connectable to both said syringe fitting and said second syringe fitting to provide fluid communication between said syringes.

20. The apparatus according to claim 1, wherein:

said hollow body is a syringe body; and said metering knob comprises a hollow cylindrical member open at both ends, having a smaller inside diameter than the inside diameter of said syringe body and a larger outside diameter than the outside diameter of said syringe body, wherein said cylindrical member defines a threaded annular space with an inner wall disposed inside the open end of said syringe body bearing against the second end of said stopper support member, wherein said threaded annular space engages the threads at the open end of said syringe body, and wherein rotation of said hollow cylindrical member in a first direction relative to said syringe body advances said stopper assembly towards said syringe fitting.

* * * * *